US006037490A

United States Patent [19]

Kabalka et al.

[11] Patent Number: 6,037,490

[45] Date of Patent: Mar. 14, 2000

[54] BORON-CONTAINING AMINO CARBOXYLIC ACID COMPOUNDS AND USES THEREOF

[75] Inventors: George W. Kabalka; Rajiv R. Srivastava, both of Knoxville, Tenn.

[73] Assignee: The University of Tennessee Research Corporation, Knoxville, Tenn.

[21] Appl. No.: 08/923,054

[22] Filed: Sep. 3, 1997

Related U.S. Application Data

[60] Provisional application No. 60/025,558, Sep. 3, 1996.

[51] Int. Cl.[7] .................. C07F 5/02

[52] U.S. Cl. .................. 562/7; 558/287; 568/3; 568/5; 568/6

[58] Field of Search .................. 562/503, 505, 562/506, 507, 7; 558/286, 287, 3, 5, 6

[56] References Cited

U.S. PATENT DOCUMENTS

| | | | |
|---|---|---|---|
| 3,135,786 | 6/1964 | Ager . | |
| 3,345,405 | 10/1967 | Burger et al. . | |
| 5,648,532 | 7/1997 | Hawthorne | 564/8 |

OTHER PUBLICATIONS

Database CAS online, 'Amino acid analogs for tumor imaging', May 15, 1997 (15.05.97)vol. 127, abstract No. 127:51001, WO 9717092A1 (Goodman et al).

CA:106:206646 ab of Inorg Chem, by Trofimenko, 26(10) pp1507–14, 1987.

CA:127:201930 ab of J Am Chem Soc 119 (34) pp 8107–8108, 1997.

Denniel, Tetrahedron Lett, vol 37, No. 29, pp 5111–5114, Jul. 1996.

CA:98:198451 ab of BE894116, Feb. 1983.

CA:118:38992, ab of Inorg Synth by Paetzold, 29, pp 54–57, 1992.

*Primary Examiner*—Gary Geist
*Assistant Examiner*—Jean F Vollano
*Attorney, Agent, or Firm*—Schnader Harrison Segal & Lewis LLP; Gerard J. Weiser

[57] ABSTRACT

Novel compounds which are useful for boron neutron capture therapy (BNCT) are disclosed. The compounds comprise a stable boron-containing group and an aminocycloalkane carboxylic acid group or a boronated acyclic hydrocarbon-linked amino carboxylic acid. Methods for synthesis of the compounds and for use of the compounds in BNCT are disclosed.

17 Claims, 3 Drawing Sheets

BORON-CONTAINING AMINO CARBOXYLIC ACID COMPOUNDS AND USES THEREOF

This is a provisional application Ser. No. 60/025,558, filed Sep. 3, 1996, which is incorporated herein by reference.

This invention was developed in the course of work supported by the Department of Energy under Contract DE-FG05-93-ER 61610.

FIELD OF THE INVENTION

The present invention relates to the field of compounds effective for the treatment of cancer. More specifically, the present invention relates to the field of boron neutron capture therapy.

BACKGROUND

Classic methods of treating neoplastic growth, by surgery, chemotherapy, and/or radiation involve a trade-off between destroying the target tumor and not killing normal cells. A tumor killing modality which does not kill normal cells is obviously desirable because the treatment could be applied as aggressively as needed to kill the tumor without the need to moderate the treatment to avoid killing non-tumor cells.

Boron neutron capture therapy, BNCT, was developed as a tumor treatment modality which is non-lethal to non-tumor cells. In BNCT, compounds containing the stable isotope boron-10 ($^{10}B$) are introduced into tumor i.e. cancer cells. The part of the body to be treated is then irradiated with neutrons, which results in the formation of high energy state $^{11}B$ atoms from $^{10}B$ atoms. Neither the neutron beams nor the $^{10}B$ are lethal to cells. However, the $^{11}B$ formed from the $^{10}B$ is in a high energy state and subsequently degenerates to $^{7}Li$ and $\alpha$ particles, which particles give rise to high energy ionizing events which kill the tumor cell. Because these particles have a path length of only about 1 cell diameter, surrounding normal tissue is not adversely affected. Therefore, BNCT basically involves providing both non-radioactive $^{10}B$ and nonionizing, low-energy level or thermal neutrons in combination in the tumor cells as described by Barth, R. F., *Cancer,* Vol. 70, No. 12, Dec. 15, 1992, Pp. 2995–3007, incorporated herein by reference.

The key to successful therapy with BNCT is to obtain a high ratio of boron in proliferating (or non-proliferating) tumor cells compared to boron in normal cells and in blood. Various boron-containing compounds have been used in the prior art to localize boron to tumor cells.

Two compounds, p-carboxybenzeneboronic acid and sodium decahydrodecaborate, have been reported to produce high ratios of boron in tumor cells compared to normal cells. BNCT treatment with these compounds, however, failed due to vascular damage caused by high blood levels of boron.

BNCT therapy with inorganic boron containing compounds, borax ($Na_2B_4O_7.10H_2O$) and sodium pentaborate ($Na_2B_{10}O_{16}.10H_2O$), was found to result in treatment failure because of the lack of localization of boron within tumor cells. A boronated porphyrin compound, 2,4-divinyl-nido-o-carboranyldeuteroporphoryin IX ("VCDP") was found to result in a tumor/normal cell boron ratio of 4:1 in mice. However, this compound is unacceptable for use for BNCT because the mortality of the mice receiving the compound was high, about 10%.

Other compounds that have been tested with varying degrees of success for their ability to localize boron in tumor cells include mercapto compounds such as $Na_2B_{12}H_{11}SH$, thiouracils, purines, pyrimidines, and boronophenylalanine (BPA). BPA has been shown to produce a ratio tumor/normal cell boron ratio of between 3 and 4 to 1 without the deleterious effects seen, for example, with porphyrin.

Other modalities which have been attempted with limited success to localize boron in tumor cells include monoclonal and polyclonal antibodies and encapsulating complexes such as liposomes, microspheres, and low density lipoproteins.

The present invention contributes to a solution to the problem of obtaining a high ratio of tumor boron/normal tissue boron, and thereby effective BNC therapy. Using the novel compounds of the invention, ratios as high as 50:1 or higher may be obtained, without harmful effects to normal tissue.

As stated above, BNCT relies upon the ability to irradiate tumor cells having a high concentration of $^{10}B$ with neutrons of suitable energy level. Such neutrons are currently provided by nuclear reactors. Nuclear reactor-derived neutrons are known as described for instance, in Barth, Cancer Vol. 70, No. 12, cited and incorporated herein above. The novel boron-containing compounds are suitable for use with irradiation by neutron beams generated by such conventional nuclear reactors and conceivably could be used with devices of emerging technologies, for example, epithermal neutron beam, californium-252, spallation and low-energy accelerator sources also as described in Barth.

As described above, BNCT is based on generating highly reactive unstable boron-11 from boron-10, the active agent in boron neutron capture therapy. Boron compounds found in nature, which can be used as starting materials for the reactions giving the compounds of the invention, generally are isomeric mixtures which contain both boron-10 and boron-11 (stable form) isotopes in a ratio of approximately 20% boron-10 and 80% boron-11. Accordingly, it is desirable to increase (or enrich) the proportion of boron-10 in the starting boron compounds (over the proportion of stable boron-11) to beyond 20%, preferably above 80%, ideally to 100% to generate a higher proportion of the highly unstable form of the isotope, boron-11. Enriched boron-10 compounds are available commercially such as from Boron Biologicals, Inc., Raleigh, N.C. or from Eagle-Pitcher Industries, Inc., Miami, Okla. Such boron-10 enriched materials are very useful in the practice of the invention.

The amino acid compounds of the invention are D- and L-racemates due to the chiral configuration of the molecule which lend themselves to resolution of the stereoisomers into the L- and D-enantiomers by methods well-known in the art or can be purchased from commercial sources. Of the enantiomers, the L-form is preferrred. Such optically pure form of the compounds of the invention, especially the respective L-forms are very useful for BNC therapy.

Methods for separation of the desired enantiomer from the stereoisomers as by enzymatic resolution are known, as reported for instance, by Coderre et al. in *Cancer Research* 47, 6377–6383 (1987) *Selective Targeting of Boronophenylalanine to Melanoma* in BALB/c Mice for *Neutron Capture Therapy,* which is incorporated herein by reference.

When the L-enantiomer of compound VIII (identified further below) separated from the racemate mixture, is tested in BNC therapy by injection in rats, high cellular uptake is observable followed by death of the cancer cells after irradiation. Comparable results are expected when the L-enantiomers of other compounds of the invention are used in BNCT.

SUMMARY OF THE INVENTION

In one embodiment, the invention provides novel chemical compounds which are boronated 1-aminocycloalkane carboxylic acids, which is preferably a boronated 1-aminocyclobutane carboxylic acid.

In another embodiment, the invention provides a method of chemically synthesizing a boronated 1-aminocycloalkane carboxylic acid, which is preferably a boronated 1-aminocyclobutane carboxylic acid, hereinafter the "ACBC series" of compounds.

In another embodiment, the invention provides a method for treating a mammalian cancer patient with boron neutron capture therapy (BNCT) using a boronated 1-aminocycloalkane carboxylic acid, preferably a boronated 1-aminocyclobutane carboxylic acid, to deliver boron into the cancer cells of the patient.

In still another embodiment, the invention provides a novel compound with a moiety containing boron in a chemically stable form in which the moiety is linked to an amino carboxylic acid ligand by an acyclic hydrocarbon having at least 2 carbon atoms, preferably 4 to 8, hereinafter the "LSK series" of compounds.

With preferred compounds of the invention, higher ratios of boron concentration in a target tumor compared to normal tissues may be achieved than with prior art compounds. Thus, tumor/normal tissue boron ratios greater than 4:1, such as 10 to 50:1 or higher may be obtained using the compounds of the invention.

In another embodiment, this invention further provides a method of chemically synthesizing a boronated acyclic hydrocarbon-linked amino carboxylic acid.

In yet another embodiment, there is provided a method of treating a mammalian cancer patient by BNCT using a boronated acyclic hydrocarbon-linked amino carboxylic acid to deliver boron into the cancer cells of the patient, then irradiating the part of the body to be treated with neutron beans which cause $^{11}B$ to be formed from $^{10}B$ atoms, which $^{11}B$ degenerate to $^{7}Li$ and α particles which give rise to high energy ionizing events which kill the tumor cells without adversely affecting the healthy cells.

DETAILED DESCRIPTION OF THE INVENTION

Figure 1:
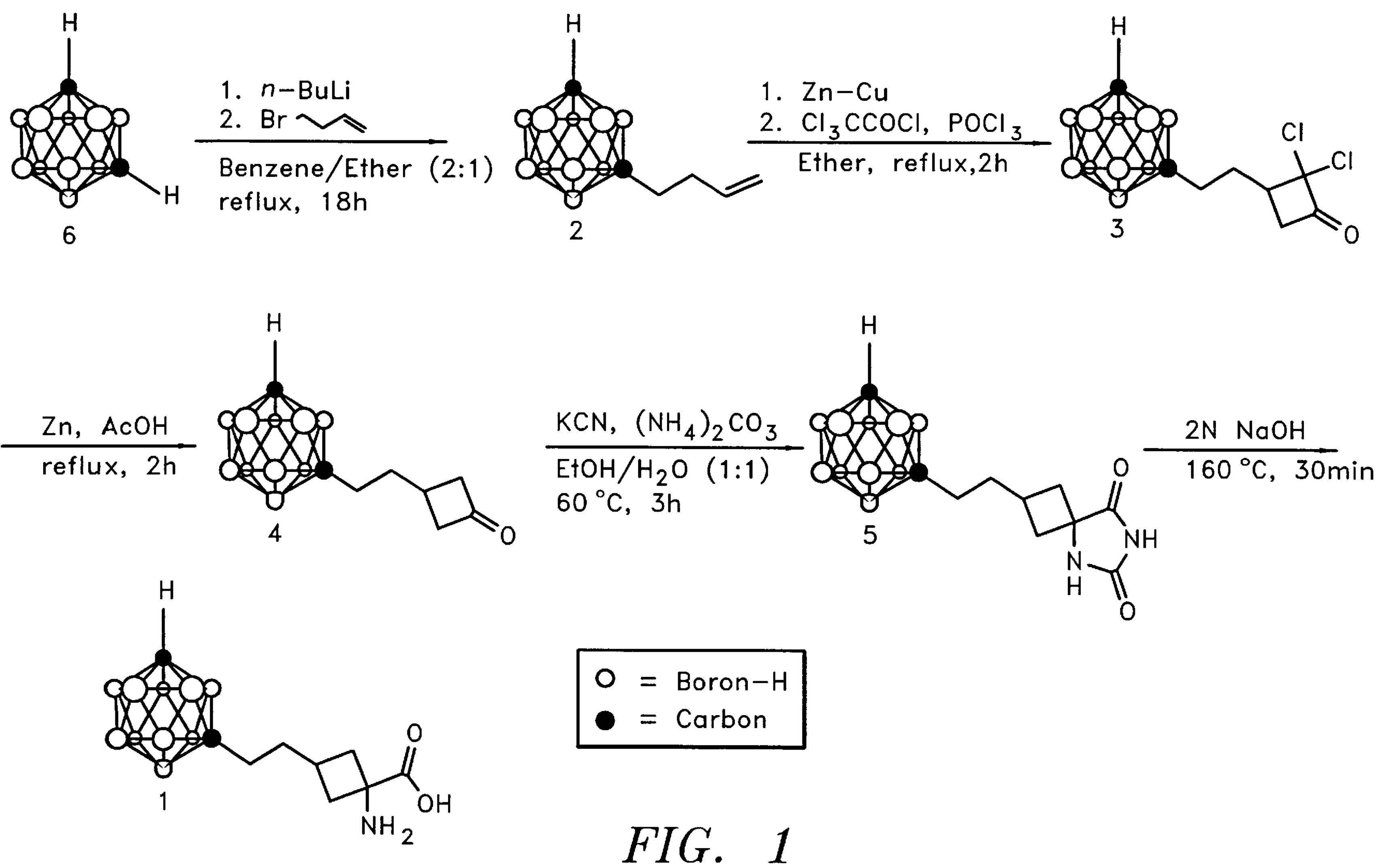
FIG. 1 shows a preferred scheme for synthesis of a boronated aminocyclobutane carboxylic acid.

Occasionally herein the following symbols are used to represent the corresponding chemical structures shown or described below, in accordance with nomenclature conventions known in the art, and especially as used in Yong, J. H., et al. *Anticancer Research* 15:2039–2044 (1995) which is incorporated herein by reference.

In accordance with the invention, there has been discovered a novel boron-containing chemical compound having the formula (V) shown below:

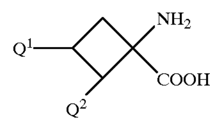

where either $Q^1$ or $Q^2$ (or both) are moieties that contain boron in a chemically stable form and are linked to an aminocycloalkane carboxylic acid, such as aminocyclobutane carboxylic acid, or amonocylopentane carboxylic acid. In one form, $Q^2$ is an alkyl boronic acid having from one to eight or more carbon atoms and $Q^1$ is hydrogen. The alkyl boronic acid ligand is of the formula —(CH2)n—B(OH)2 wherein "n" is an integer from 1 to 12 carbon atoms, or higher, preferably 1 to 8.

The boron may be in the form of a monoboron or a polyborono species, for example as a closo- and nido-polyhedral borane, carborane, boronic acid, boronic ester (generally a lower alkyl ester), boron hydride, and related complexes. An example of a suitable boronic acid derivative has the formula (VI) shown below:

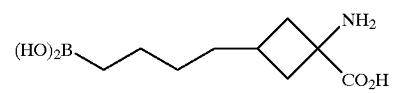

In a preferred embodiment, the boron complex is a carborane, the formula (VII) of which is shown below:

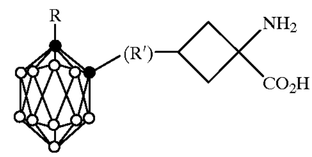

In this embodiment (VII) $Q^1$ comprises an ortho-carborane, $Q^2$ is H, R represents hydrogen, or any stable organic group like a hydrocarbon group, including alkyl, alkenyl, alkynyl, aryl, alcopolyol, saccharide, peptide, or a thiol group, and R' represents hydrogen, or any alkyl, alkenyl, alkynyl, or aryl group, wherein alkyl, alkenyl, or alkynyl are preferably 1 to 6 carbon atoms long, and aryl (substituted or not) is preferably of 6 carbon atoms.

The boronoaryl substituted aminocycloalkyl carboxylic acids of the invention include the meta- and para-carboranes. Representative of the boron-containing amino cyclo alkyl carboxylic acids are 1-amino-3-[2-(1,7-dicarba-closo-dodecacaboran(12)-1-yl) ethylcyclobutane carboxylic acid; 1-amino-3-[2-(7-(2-hydroxyethyl)-1,7-dicarba-nido-dodecacaboran(12)-yl)ethyl]cyclobutanecarboxylic acid (ACBC); 1-amino-3-[2-(7-(2-hydroxyethyl)-1,7-dicarba-nido-dodecacaboran(12)-ylethyl]cyclobutanecarboxylic acid (VIII); amino-3-[2-(1-methyl-1,2-dicarba-closo-dodecacaboran(12)-1-yl)ethyl]cyclobutanecarboxylic acid (IX); and 1-amino-3[2-(7-(2-hydroxyethyl)-1,7-dicarba-closo-dodecacaboran(12)-yl ethyl]cyclobutanecarboxylic acid (X), compounds VIII, IX and X being shown below, respectively:

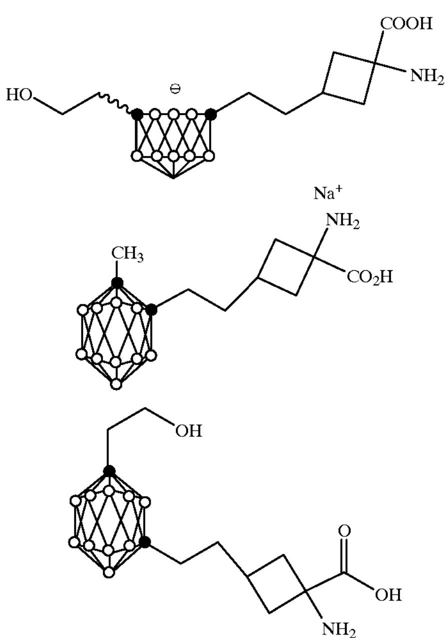

The optically pure L- and D-forms of the above-identified borono-compounds are obtainable, the L-enantiomers being preferred.

Noteworthy is that with the carborane compounds of the invention a concentration in the cancer cell is attained which is in excess of that of the best currently known compound, para-(ortho-carboran-yl)-phenylanaline, (CBPA) reported to be currently in clinical trials in the U.S. It is essential that the amount of boron in the cancer cell exceeds that of boron in normal tissue and blood by at least a factor of 3. The greater ratio the better. CBPA is reported to exhibit a ratio of about 4:1. Carborane compounds of the invention have been observed to reach ratios of over 4:1, like 7:1, 10:1 and as noted above, even higher without harmful effects to normal tissue.

Also noteworthy is that the non-cyclic amino acids carboranes compounds of the invention, typified by 2-amino-5-[2-methyl]-1,2-dicarba-closo-dodecacarboran(12)-1-yl] pentane carboxylic acid (also named 5-(1-methyl-o-carboranyl)-1-amino-pentanoic acid) (LSK 1–38) exhibits advantageous properties over CBPA, as reported in the literature, for instance in Evaluation of in Vitro Cytotoxicity of Carboranyl Amino Acids, their Chemical Precursors and nido Carboranyl Amino Acids for Boron Neutron Capture Therapy by Jing-Hong Yong et al. in *Anticancer Research* 15:2039–2044 (1995).

The boron-containing compounds of the invention may be synthesized by several different methods, for example which comprises:

a) alkylating a boron-containing compound by reacting the group with 4-bromo-butene, e.g. a methyl-o-carborane, b) reacting the alkylated boron-containing compound with dichloroketene to obtain a dichloroketone of the alkylated boron-containing compound, c) reducing the dichlokoketone to remove the chlorines and to obtain an alkylated boron-containing ketone, d) reacting the ketone with KCN and $(NH_4)_2CO_3$ to obtain an alkylated boron-containing hydantoin, and e) hydrolyzing, preferably by acid hydrolysis, the hydantoin to yield the boronated 1-aminoalkane carboxylic acid.

The preferred boron-containing amino carboxylic acid, an aminocyclobutane carboxylic acid, is preferably synthesized by the scheme shown diagrammatically in FIG. 1. The synthetic scheme is exemplified to produce a carboranyl substituted 1-aminocyclobutane carboxylic acid. However, the synthetic scheme may be applied to produce a 1-aminocyclobutane carboxylic acid substituted with virtually any boron containing group and may be utilized to produce an aminocyclopentane carboxylic acid.

As shown in FIG. 1, a boron containing group, such as methyl-o-carboranyl lithium 6 was reacted with 4-bromo-butene in the presence of benzene/ether solution to yield an alkylated meta-carboranyl lithium 2. Dichloroketene, generated from trichloroacetyl chloride in the presence of a Zn—Cu couple and phosphorus oxychloride, was reacted with the alkylated meta-carboranyl lithium 2 to obtain dichlorocyclobutanone 3. The dichlorocyclobutanone 3 was reduced with zinc dust in 80% acetic acid at 45° C. to yield a cyclobutanone, such as an alkylated meta-carboranyl cyclobutanone 4. The cyclybutanone was reacted with KCN and $(NH_4)_2CO_3$ and ethyl alcohol, at 60° C. to generate a hydantoin 5. The hydantoin was base hydrolyzed using 2 N NaOH at 160° C. and refluxed for 24 hours to generate the boron containing amino acid 1, which may be isolated.

Alternatively, the boron-containing compounds of the invention may be synthesized by other known reactions to produce carboranyl substituted with aminocyclobutane carboxylic acid.

In another preferred embodiment the boron-containing compound is a carborane ligand linked to an aminocarboxylic acid by an acyclic hydrocarbon of from 1 to 12 or more carbon atoms, such as 18, and preferably 4 to 8 carbon atoms. The carborane ligand can have the same chemical structure as described for $Q^1$ and $Q^2$, above. Particular preference is given to the methyl-substituted ortho-carborane acyclic hydrocarbon linked amino carboxylic acid of formula XI.

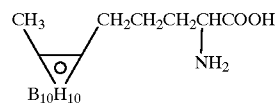

Meta- and para-carborane structures are also possible for inclusion in the acyclic hydrocarbon-linked amino carboxylic acid.

Figure 2:
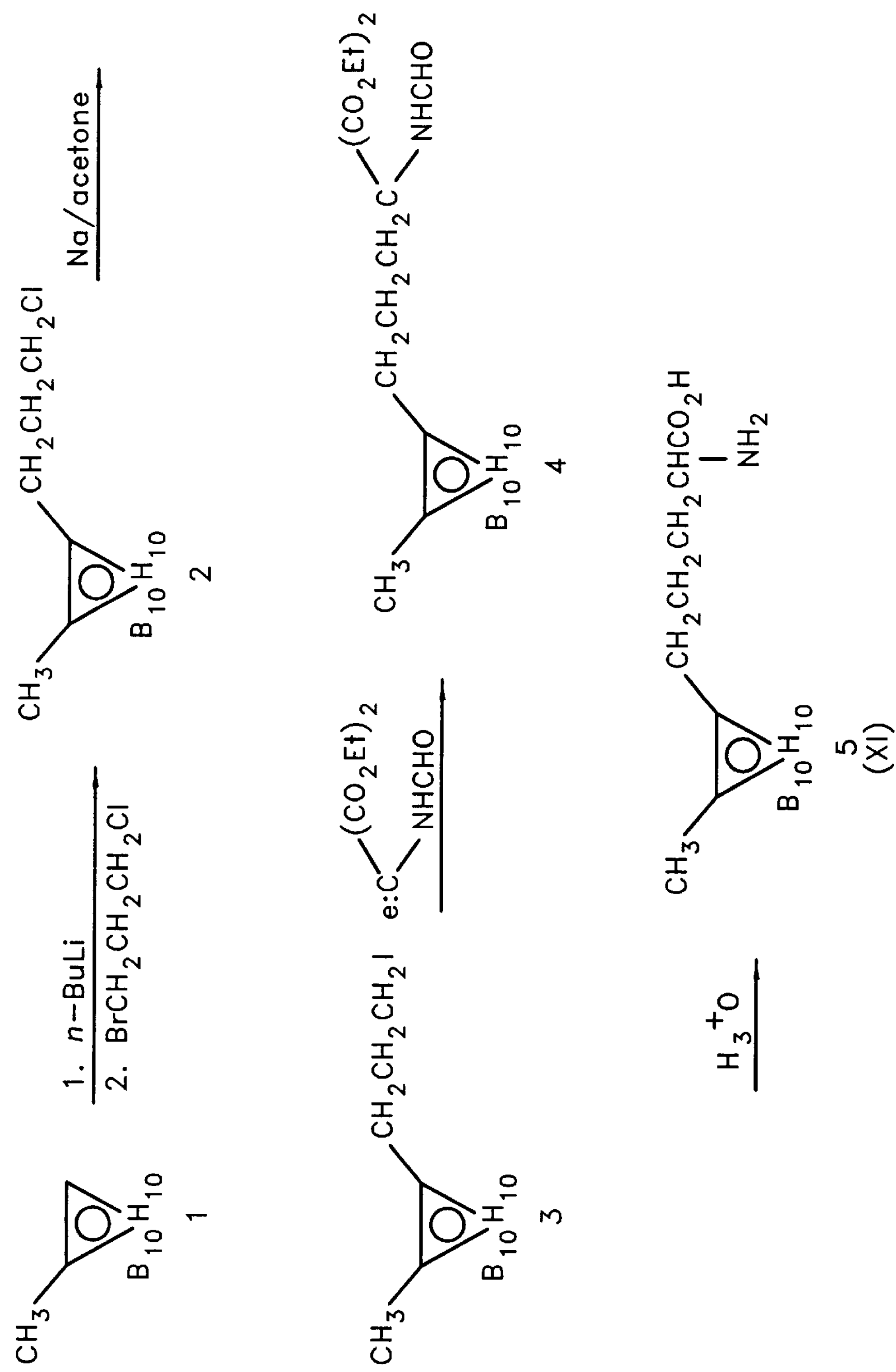
FIG. 2 shows a preferred scheme for synthesis of a boronated acyclic hydrocarbon-linked amino carboxylic acid.

A method of synthesizing the compound XI is shown schematically in FIG. 2. The procedure is more fully described in Example 3, below.

The boron-containing compounds of this invention are suitable for use in introducing boron into many types of cancer cells proliferating (or not) generally human cancer cells for human therapy and other mammals' cells for veterinary therapy. Representative tumor types include Hodgkin's lymphomas; lymphocytic leukemias; multiple melanoma; neuro blastoma; breast, ovary, lung, cervix and testis tumors; malignant melanoma; and soft-tissue and osteogenic sarcomas, as are described more completely in *Goodman and Gilman's The Pharmacological Basis of Therapeutics,* 8th ed., McGraw-Hill, Inc., N.Y., 1993, incorporated herein by reference.

Of particular interest is the use of the compounds of the invention in the treatment of primary and metastatic brain tumors, specifically glioblastoma multiforme and malignant melanomas for which, it is reported, there currently is no effective therapy.

According to the treatment method of the invention, the novel boron-containing compounds of the invention are used with BNCT as disclosed further herein. A selected boron-containing compound is administered to the patient, preferably by percutaneous injection, for example intraperitoneally. The compound enters the patient's vascular system and is allowed to localize within the tumor, which is then irradiated.

The therapy prescribed may provide for sequential treatment with the same or different compounds of the invention or as a "cocktail" of such compounds, or in conjunction with conventional compounds.

In a preferred embodiment, the compound of the invention is combined with a pharmaceutically acceptable carrier, such as a physiologically buffered saline solution, like lactated Ringers, and is injected intravenously or intraarterially into a cancer patient. Dosage of the compound is an amount necessary to obtain an effective level, such as about 25 to 40 parts per million of boron-10 in the cancer cells. Generally, about 5 to 40 grams, typically about 25 grams, of the compound is injected to the patient. About two hours following administration of the boron-containing compound, the patient is irradiated with a neutron beam which converts $B^{10}$ to the unstable isotope $B^{11}$, in order to exert its lethal effect on the cells of the patient's cancer cells. Normally, non-neoplastic tissue is not affected.

The invention includes the pharmaceutically acceptable inorganic and organic water-soluble salts of the compounds of the invention including the alkali and alkaline earth metal salts (such as sodium, magnesium; the chloride, etc.); the esters and ethers such as the acetate (wherein the alkyl group is preferably lower alkyl).

The invention is now illustrated by non-limiting, representative examples, in which the following general methods were employed:

EXAMPLE 1

General Methods

All solvents were reagent grade and were distilled from appropriate drying agents under a nitrogen atmosphere prior to use. Diethyl ether was distilled from sodium benzophenone ketyl; benzene was distilled from calcium hydride and stored under nitrogen. m-Carborane was purchased from Dexsil Corporation (Hamden, Conn.) and purified by sublimation. All other chemicals were purchased from Aldrich Chemical Co. (Milwaukee, Wis.) and used as received.

Column chromatography was performed using silica gel (60 A°, 230–400 mesh) obtained from Baxter Co. (McGaw Park, Ill.). Reverse-phase column chromatography was performed utilizing octadecyl functionalized silica gel obtained from Aldrich Chemical Co. (Milwaukee, Wis.). Analytical thin layer chromatography was performed on 250 micron silica plates obtained from Analtech Inc. (Newark, Del.) and were visualized by phosphomolybdic acid, palladium chloride and silver nitrate solutions.

Melting points are uncorrected. Infrared spectra were obtained either neat or as Nujol mulls. $^{1}H$ NMR and $^{13}C$ NMR spectra were recorded on a Bruker AC 250 at 250.13 and 62.89 Mz respectively. $^{11}B$ NMR ($^{1}H$-decoupled)spectra were obtained on a Bruker AMX-400 at 128.38 Mz. Chemical shifts for $^{1}H$ and $^{13}C$ NMR spectra were referenced to $Si(CH_3)_4$ and measured with respect to the residual protons in the deuterated solvents. In the case of $^{11}B$ NMR, chemical shifts were measured with reference to external $BF_3{\bullet}OEt_2$. Resonances observed upfield of the reference ($BF_3{\bullet}OEt_2$) were assigned negative chemical shift value. Microanalysis were performed by Galbraith Laboratories Inc., Knoxville, Tenn. HR-FAB-MS (M+1) were obtained on a ZAB-EQ instrument in a glycerol matrix.

The example can be better understood with reference to FIG. 1 to which the reference numerals refer.

A. Synthesis of 4-m-carboranyl-1-butene (2)

A three-necked round bottomed flask equipped with an addition funnel, reflux condenser and argon balloon was charged with m-carborane (35 mmol, 5.0 g) and a mixture of benzene (70 ml) and ether (35 ml). The reaction mixture was cooled to 0° C. and butyllithium (38 mmol, 24 ml of 1.6 M solution in hexane) was added via a syringe over a period of 10 min. and the mixture allowed to stir at room temperature for 30 min. The reaction mixture was then cooled to 0° C. and to it was added a mixture of 4-bromobutene (39 mmol, 3.9 ml) in a mixture of benzene (10 ml) and ether (5 ml). The reaction mixture was then refluxed at 90° C. in an oil bath for 18 h, cooled to room temperature, and quenched with water (2 ml). The solution was transferred to a separatory funnel and washed successively with water (2×20 ml) and brine (1×20 ml). The organic layer was dried over anhydrous $MgSO_4$, filtered and concentrated under reduced pressure using a rotoevaporator. After drying at 50° C. at 0.2 mm Hg, a colorless liquid (7.1 g) was obtained. The crude product was purified by column chromatography using silica gel (27×4 cm, hexane as eluent) to yield 2 as a colorless liquid (5.8 g, 84% yield); Rf=0.76 (hexane, thin layer chromatography); $^{1}H$ NMR ($CDCl_3$) δ 5.67 (m, 1 H), 5.00 (m, 2 H), 2.91 (s, 1 H), 2.03 (m, 4 H); $^{13}C$ NMR ($CDCl_3$) δ 136.13, 115.74, 75.32, 54.85, 36.06 33.77; $^{11}B$ ($CDCl_3$) δ −1.81 (s, 1 B), −8.71 (s, 4 B), −11.32 (s, 3 B), 13.27 (s 2 B); IR (neat) 3064, 2981, 2919, 2854, 2598, 1735, 1641, 1436, 1244, 1046, 994, 924, 908, 735 $cm^{-1}$. HR-FAB-MS (M+H; obtained in glycerol matrix) Calcd. for $C_6H_l B_{10}$: 198.24 1. Found: 198.243.

B. 3-[2-(1,7-Dicarba-closo-dodecacaboran(12)-1-yl) ethyl] cyclobutanone (4)

The synthesis of this compound was achieved in two steps. 2,2-dichloro-3-[2-(1,7-dicarba-closo-dodecacaboran (12)-1-yl)ethyl]cyclobutanone 3 was synthesized from 4-m-carboranyl-1-butene (2) and then the haloketone was treated with zinc and acetic acid to yield the desired compound 4.

A 250 ml, three-necked, round bottomed flask equipped with a reflux condenser and an argon balloon was charged with 4-m-carboranyl-1-butene (2) (29 mmol, 5.8 g ) and diethyl ether (100 ml). Freshly prepared Zn—Cu couple (174 mmol, 22.5 g ) was added followed by trichloroacetyl chloride (64 mmol, 7.2 ml) and phosphorous oxychloride (64 mmol, 5.9 ml). After stirring the mixture at room temperature for 10 min., it was refluxed under an argon atmosphere. After 2 h at reflux, the reaction was cooled to room temperature and filtered through a pad of Celite. Additional ether (50 ml) was used to transfer the material. The solvent was removed under reduced pressure using a rotatory evaporator and the viscous 2,2-dichloro-3-[2-(1,7-dicarba-closo-dodecacaboran(12)-1-yl)ethyl]cyclobutanone (3) was dried under high vacuum (0.2 mm Hg at 50° C.).

The crude 2,2-dichloro-3-[2-(1,7-dicarba-closo-dodecacaboran(12)-1-yl)ethyl]cyclobutanone (3) was dissolved in glacial acetic acid (50 ml) in a 100 ml round-bottomed flask, fitted with a reflux condenser, containing zinc dust (10 g, excess). The mixture was stirred at room temperature for 20 min then it was refluxed for 2 h. TLC indicated the complete disappearance of the starting material. The reaction was cooled to room temperature and filtered through a pad of Celite. Additional ethyl acetate (100 ml) was used to wash the Celite pad and transfer the material from the round-bottomed flask. The solvent was removed under reduced pressure using a rotoevaporator. The viscous mass was dissolved in ethyl acetate (100 ml) placed in a separatory funnel, and then washed sequentially with water (2×20 ml), saturated sodium bicarbonate (2×20 ml), water (2×20 ml), and brine (1×20 ml). The organic layer was dried over anhydrous magnesium sulfate, filtered, and concentrated under reduced pressure using a rotoevaporator. The reaction yielded a viscous material (8.9 g) which was purified by column chromatography using silica gel (30×4 cm, 10% ethyl acetate in hexane) to yield 4 as a colorless oily product [(3.1 g, 44% overall yield based on 4-m-carboranyl-1-butene (2)]: Rf=0.56 (15% ethyl acetate in hexane, thin layer chromatography); $^{1}$H NMR ($CDCl_3$) δ 3.16 (m, 2 H), 2.93 (s, 1 H), 2.64 (m, 2 H), 2.24 (m, 1 H), 1.96 (m, 2 H), 1.68 (m, 2 H); $^{13}$C NMR ($CDCl_3$) δ 206.7, 75.4, 54.9, 52.4, 36.3, 35.6, 23.4; $^{11}$B ($CDCl_3$) δ −1.91 (s, 1 B), −8.66 (s, 4 B), −11.42 (s, 3 B), −13.22 (s, 2 B); IR (neat) 3060, 2946, 2929, 2868, 2596, 1784, 1452, 1385, 1104, 1062, 1008, 729 cm$^{-1}$. Anal. Calcd. for $C_8H_{20}B_{10}O$: C, 39.98; H, 8.39; B, 44.98. Found: C, 40.44; H, 8.28; B, 43.63.

C. Hydantoin of 3-[2-(1,7-dicarba-closo-dodecacaboran (12)-1-yl) ethyl]cyclobutanone (5)

A 15 ml Ace pressure tube was charged with 3-[2-(1,7-dicarba-closo-dodecacaboran(12)-lyl)ethyl]cyclobutanone (4) (0.42 mmol, 0.10 g), aqueous ethanol (50%, 2 ml), potassium cyanide (0.46 mmol, 30 mg), and ammonium carbonate (1.0 mmol, 0. 10 g). The reaction vessel was sealed and heated at 60° C. in an oil bath for 3 h. A white precipitate formed. The reaction vial was cooled to room temperature and the cap unscrewed carefully in a fume hood. The reaction mixture was quenched with aqueous acetic acid (2 ml of a 30% solution in water). The solvent was removed under reduced pressure using a rotary evaporator and the resultant white solid taken up into ethyl acetate (50 ml) in a separatory funnel and washed sequentially with water (2×10 ml) and brine (1×10 ml). The organic layer was dried over anhydrous magnesium sulfate, filtered, and concentrated under reduced pressure. A white solid was obtained (0.27 g) and this was purified by column chromatography using silica gel (20×4 cm, 10% methanol in methylene chloride) to yield 5 as a white solid (0.11 g, 84% yield): Rf=0.65 (10% methanol in methylene chloride, thin layer chromatography); mp 332–334° C. (with decomposition); $^{1}$H NMR ($CD_3OD$) δ 3.48 (s, 1 H), 2.53 (m, 2 H), 2.25 (m, 3 H), 1.89 (m, 2 H), 1.64 (m, 1 H), 1.51 (m, 1 H); $^{13}$C NMR (DMSO-db) δ 178.59, 155.82, 59.06, 57.54, 56.20, 37.73, 36.73, 36.48, 33.34, 25.46; $^{11}$B ($CD_3OD$) δ −1.36 (s, 1 B), −8.06 (s, 4 B), −10.66 (s, 2 B), −11.56 (s, 1 B), −12.24 (s, 2 B); IR (nujol) 3207, 3040, 2949, 2920, 2850, 2755, 2597, 1761, 1734, 1435, 1305, 1120, 778, 765, 727, 643 cm$^{-1}$. Anal. Calcd. for $C_{10}H_{22}B_{10}O_2N_2$:C, 38.70; H, 7.14; N, 9.03; B, 34.83. Found: C, 38.31; H, 6.73, N, 8.70; B, 33.51.

D. 1-Amino-3-[2-(1,7 dicarba-closo-dodecacaboran(12)-1-yl)ethyl]cyclobutanecarboxylic acid (1)

The hydantoin of 3-[2-(1,7-dicarba-closo-dodecacaboran (12)-1-yl)ethyl]cyclobutanone (5) (0.64 mmol, 0.20 g) was placed in a 15 ml Ace pressure tube along with a solution of sodium hydroxide (5 ml of 2 N NaOH). The reaction mixture was heated to 160° C. in an oil bath for 30 min. It was then cooled to room temperature and opened carefully. TLC indicated the disappearance of the starting hydantoin. The reaction mixture was acidified using concentrated hydrochloric acid and the volatile solvents removed under reduced pressure using a rotary evaporator. The white solid obtained was purified by column chromatography using octadecyl functionalized silica gel (22×2 cm, 80% methanol in water). The product 1 was obtained as a white solid (0. 15 g, 82% yield): Rf=0.55 (in a mixture of butanol, water, and acetic acid in ratio of 10:1:0.5); mp compound turns brown (without melting) at 201° C.; $^{1}$H NMR ($CD_3OD$) δ 3.49 (s, 1 H), 2.63 (m, 2 H), 2.40 (m, 3 H), 1.89 (m, 2 H), 1.61 (m, 2 H); $^{13}$C NMR ($CD_3OD$) δ 176.3, 77.5, 56.9, 38.4, 37.5, 36.8, 36.0, 35.2, 29.0; $^{11}$B ($CD_3OD$) δ −1.45 (s, 1 B), −8.11 (s, 4 B), −10.70 (s, 2 B), −11.42 (s, 1 B), −12.29 (s, 2 B); IR (nujol) 4000, 3434, 3060, 2947, 2909, 2849, 2598, 2294, 1719, 1677, 1566, 1457, 1377, 1269, 1233, 1183, 1139, 1072, 1009, 728 cm$^{-1}$. Anal. Calcd. for $C_9H_{23}B_{10}O_2N$: C, 37.60; H, 8.07; N, 4.87; B, 38.32. Found: C, 36.54; H, 7.96; N, 5.24; B, 35.94. HR-FAB-MS (M+H; obtained in glycerol matrix) Calcd. for $C_9H_{24}B_{10}O_2N$: 286.282. Found: 286.284.

EXAMPLE 2

Synthesis of 1-amino-3-[2-(7-(2-hydroxy ethyl)-1,7-dicarba-nido-dodecacaboran(12)-yl)ethyl] cyclobutanecarboxylic acid.

Figure 3:
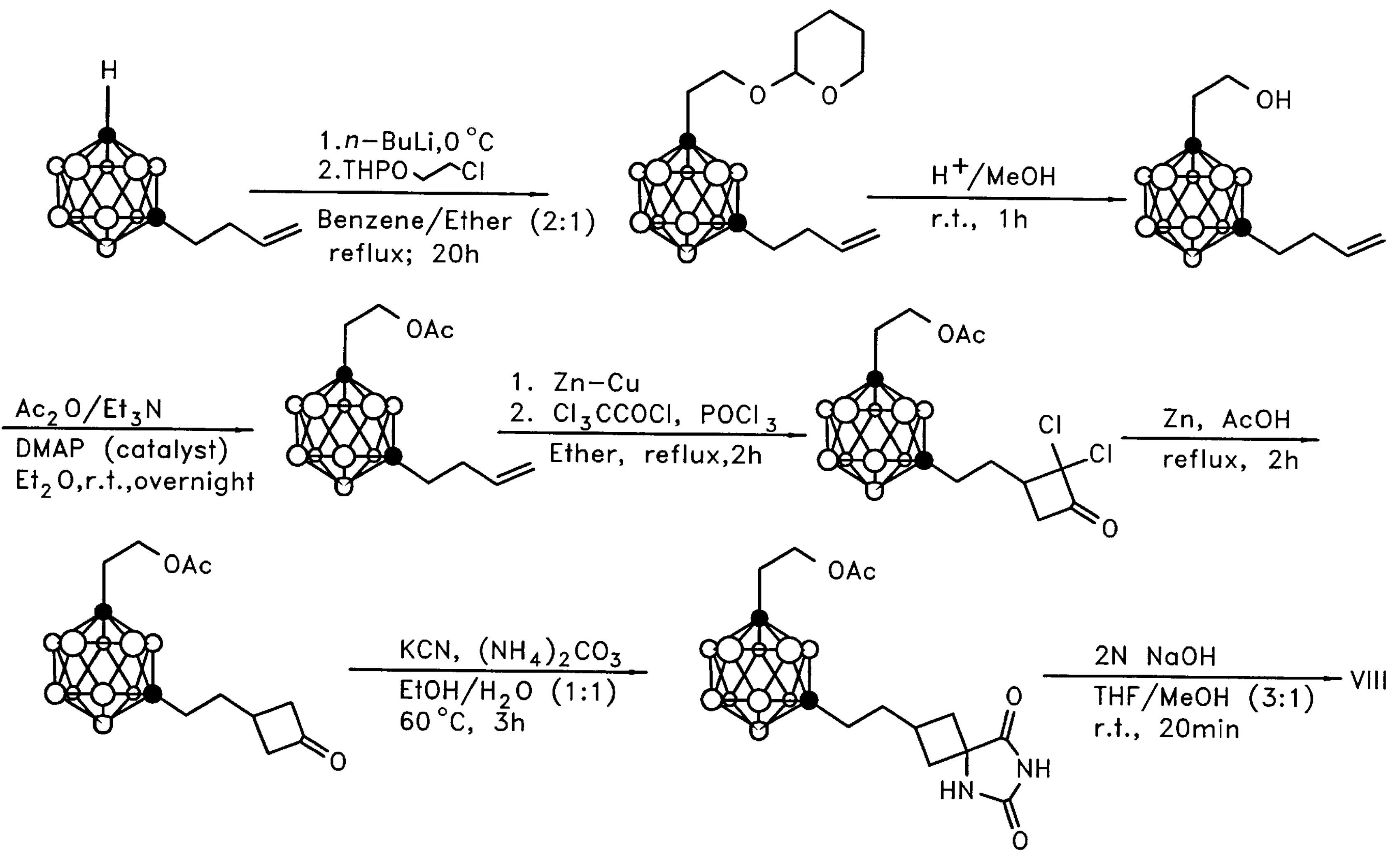
FIG. 3 shows a preferred scheme of synthesis of another boronated amino cyclic butane carboxylic acid.

The above-named amino cyclobutane carboxylic acid has the formula VIII. This compound was synthesized by the procedure outlined in FIG. 3.

EXAMPLE 3

Synthesis of 5-[2-amino-methyl-1,2-dicarba-closo-dodecacarboran(12)-1-yl]pentane carboxylic acid.

The borane-containing compound (XI) was synthesized according to the following procedure which can better be understood with reference to FIG. 2. Reference numerals refer to the symbols in this Figure.

A. Synthesis of 1-methyl-2-chloropropyl-o-carborane (2)

To a solution of 1-methyl-o-carborane, 1, (316 mg. 2.0 mmol), 5 ml of ether and 10 ml of benzene, 1.4 ml of n-BuLi (1.6 M in hexanes) was added dropwise at 0° C. The solution was stirred for 2 hours at 0° C. and then 1-bromo-3-chloropropane (450 mg, 2.9 mmol) was added at 0° C. The reaction mixture was heated to reflux for 2 days and the solution was washed sequentially with 5% aqueous HCl (10 ml); water (10 ml) and concentrated. The crude mixture was purified by column chromatography (alumina, hexane to 15% ethyl acetate in hexanes) to give 290 mg (1.24 mmol, 62%) of 2.

B. Synthesis of 1-methyl-2-iodopropyl-o-carborane (3)

A mixture of 1-methyl-2-chloropropyl-o-carborane, 2, (235 mg, 1.0 mmol) sodium iodide (225 mg, 1.5 mmol) and 5 ml of acetone was heated to reflux for 6 hours. The solution was filtered, concentrated and purified by column chromatography (alumina, hexanes) to give 254 mg. (0.78 mmol, 78%) of 1-methyl-2-iodopropyl-o-carborane.

C. Synthesis of diethyl (1-Methyl-o-carboranyl)propyl (formamido)malonate (4)

Sodium (78 mg, 3.4 mmol) was added to 12 ml of absolute ethanol and stirred for 30 min. To this cooled solution (0° C.), diethyl formamido malonate (623 mg, 3.1 mmol) was added in one portion and the stirring was continued for 30 min. A solution of 1-methyl-2-iodopropyl-o-carborane, 3, (1.0 g, 3.1 mmol) in 2 ml of ethanol was added dropwise and allowed to stir for 2 days at room temperature. The mixture was heated to reflux for 2 hr and the solution was concentrated, and purified by column chromatography (silica gel, 5% ethyl acetate in hexanes) to give 470 mg (1.2 mmol, 39%) of 4.

D. Synthesis of 2-amino-5-[2-methyl-1,2-decarba-closo-dodecacarboran(12)-1-yl]pentane carboxylic acid(5)

A solution of diethyl (1-methyl-o-carboranyl)propyl (formamido) malonate, 4, (120 mg, 0.31 mmol) in 2 ml of 6 N HCl was heated to reflux for 2 hrs. After 20 min., acetic acid (1 ml) was introduced and the solution was heated to reflux for an additional 4 hrs. The solvent was removed and the residue was crystallized from aqueous ethanol to give 54 mg (0.2 mmol, 64%) of 5.

By replacing the methyl-2-iodopropyl reactant by an appropriate longer or shorter iodo (or equivalent substituted alkyl reactant), there is obtained the corresponding borane derivative of LSK 1-38, like the 1-aminooctanoic compound.

The possibility is not excluded that the carboramyl moiety be substituted by lower alkyl (like isobutyl, propyl, ethyl, etc.) as opposed to by methyl.

EXAMPLE 4

Synthesis of X (1-amino-3-[2-(7-(2-hydroxyethyl)-1,7-dicarba-closo-dodecacarboran(12)-yl) ethyl] cyclobutanecarboxylic acid. The synthesis of compounds X is performed as described for compounds VIII (FIG. 2, Example 2) except that the final hydrolysis step (last equation shown in FIG. 2) is carried out by heating the hydantoin with concentrated hydrochloric acid at 160° C. for 20 minutes.

EXAMPLE 5

The water soluble sodium salt of the boron containing amino carboxylic compound VIII, was injected into four mice bearing human glioblastoma multiforme (brain) tumors on their hind quarter. One animal was sacrificed after 3 hours, 6 hours, 12 hours, and 24 hours and tissue samples were taken from the tumor, normal brain tissue, blood and muscle. At three hours the tumor contained 52 parts per million of boron and the normal brain contained only 7.6 ppm (a ratio of nearly 7:1). At twelve hours the tumor boron concentration was 37 ppm and the normal brain concentration was 3.7 ppm (a ratio of 10:1).

Upon irradiation with neutrons, α particles will be generated that will kill the tumor cells.

When these tests are repeated with other compounds of the invention, high concentration of the boron compound in the cell is obtained.

EXAMPLES 6 AND 7 AND COMPARATIVE EXAMPLES 1 and 2

The cellular toxicities of boronated compounds 1-amino-3-[2-(1,7-dicarba-closo-dodecacaboran(12)-1-yl)ethyl] cyclobutanone "ACBC" (Example 5); 5-(1-methyl-ortho-carboranyl)-1-aminopentanoic acid "LSK 138" (Example 6); and two boron-containing nucleosides CDU-4 (Comparative Example 1) and CN-V-264 (Comparative Example 2) were determined. Each of the boronated compounds was introduced into a dividing culture of A549 lung cancer cells of known cell number at concentrations of 1.25, 2.5, 5, 10, 15 and 20 μg $^{10}$B/ml. The cells were plated for undisturbed colony growth for seven to ten days and a survival assay was performed. Colonies were washed with isotonic saline and absolute methanol before staining with Giemsa and standard colony counting.

Irradiation with Neutrons

The irradiation was performed by known techniques. The $^{252}$Cf isotope is a useful source of neutrons for BNCT (Hatanaka 1991, A). The neutron spectrum and beam characteristics are similar to those of reactor fission sources with a most probable energy of about 1 MeV. A 50 mg source of $^{252}$Cf moderated by water provides a source of $1\times10^9$ thermal neutrons/cm$^2$/sec at a distance of 3 cm (personnel communication Dr. R. Martin). The half-life of $^{252}$Cf is 2.65 years, thus this provides a simple and reliable source of neutrons for BNCT in locations without suitable nuclear reactors.

This work was performed using sealed $^{252}$Cf source capsules in a hot cell without transferable radioactive contamination using a double tube arrangement which contained 1.0 ml of A 549 lung cancer cells (maximum cell number $2\times10^6$ cells/ml and minimum cell number $2\times10^3$ cells/ml). The cancer cells were exposed to approximately $2\times10^8$ thermal neutrons per cm$^2$ per second from 30 mg of $^{252}$Cf. The flux of neutrons was determined by the irradiation of manganese wire and subsequent analysis of activation. The duration of exposure of cells was 30 sec. 1, 1.5, 2.0 and 4.0 minutes for control groups and boronated compounds. Following radiation exposure, the A 549 lung cancer cells were placed on ice for subculturing and cell survival studies.

Chemical Analysis

The measurement of total cellular boron was made using inductively coupled mass spectrometry. Boron concentrations were measured against a calibration curve generated with a series of NIST traceable standards. Yttrium and indium (20 ng/ml) internal standards were employed to correct for drift. Analyte recoveries were monitored by the addition of boron spikes (20 ng/ml) to the samples. Analyte response was corrected accordingly. Finally, a boron standard of 60 ng/ml was utilized to ensure continued calibration. In nitric acid solutions containing boron, the detection limit was at 0.4 ppb. In similar solutions containing dissolved organic cellular debris, the boron detection limit was determined to he 1.0 ppb. The lung cancer cell culture with boron exposed cells was washed by centrifugation twice, and the supernate was removed by suction prior to chemical analysis. Thus, boron detected by the chemical analysis was of intercellular boron that had undergone cellular transport not extracellular boron from the culture media. In order to obtain an accurate measurement of total boron, the biological material was chemically digested (R. Barth et al., Anal. Chem., Vol. 63, 890–893 (1991) and W. Porschen et al., Environ. Biophys., Vol. 26, 209–218 (1987)) to free all boron from organic interference. All the reagents for sample preparation were analytical grade. Concentrated nitric acid (1–2 ml) and 30% hydrogen peroxide was applied to the cells.

The nitric acid-hydrogen peroxide cocktail was allowed 96 hours for cellular digestion in tubes that facilitated the venting of generated gases. Intermittent stirring was also performed on the sample tubes. All contents were transformed to boron-free tubes and the final volume was adjusted with distilled water to a 10 ml total volume for each sample tested.

Boron Toxicity

The seven day experiments to determine boronated compound toxicity in A549 lung cancer cells is shown in Table 1. All boronated compounds displayed toxic effects in cell culture at levels as low as 1.25 μg B/ml. The amino acids LSK and ACBC suppressed all cell growth at levels above 10 μg B/ml compounds LSK and ACBC respectively. The nucleosides CN-V-264 and CDU-4 suppressed all cell growth at levels above 2.5 μg B/ml.

TABLE 1

| μgB/ml | ACBC | LSK | CDU-4[1] | CN-V-264[2] |
|---|---|---|---|---|
| 1.25 | 39 | 50 | 22 | 10 |
| 2.5 | 14 | 33 | 69 | 4 |
| 5.0 | 8 | 18 | 0 | 0 |
| 10.0 | 8 | 2 | 0 | 0 |

TABLE 1-continued

| μgB/ml | ACBC | LSK | CDU-4[1] | CN-V-264[2] |
|---|---|---|---|---|
| 15.0 | 0 | 0 | 0 | 0 |
| 20.0 | 0 | 0 | 0 | 0 |

1. CDU-4 is 5-(4'-carboranyl-1-butynyl) uridine.
2. CN-V-264 is 5-(5'-carboranyl-1-pentynyl) deoxyuridine.

Chemical analysis by inductively coupled plasma mass spectroscopy provided cellular uptake data of boronated compounds as shown in Table 2. Calculations of the average number of hits per cell, at four minute exposures (fluence of 4.8×109 n/cm2), resulting in nuclear reactions are also given in Table 2.

The intercellular boron concentration observed in these experiments were comparable to the results published by other researchers. The greatest cellular uptake was observed with the cyclic amino acid ACBC. This amino acid was almost two orders of magnitude greater in uptake than the other compounds tested. LSK-138 provided the next highest cellular uptake. The nucleosides CN-V-264 and CDU-4 were the lowest in cellular uptake. The minimum amount of the $^{10}B$ isotope necessary for BNCT at the cellular level is $10^9$ atoms of $^{10}B$ per cell (Fairchild and Bond 1985, which is incorporated herein by reference). These boronated compounds achieved this intercellular level of $^{10}B$ concentration with the use of unenriched chemical preparations.

Enriched boronated compounds are within the contemplation of the invention.

All boronated compounds tested worked as agents in boron neutron capture reactions. Cell survival data was calculated from semi-log plots and subjected to a regression analysis to obtain an X coefficient (kill constant) for each compound. Absolute value of the kill constants were found to be as follows: ACBC 2.71, LSK1-138 2.64, CN-V-264 2.88 and CDU-4 2.87. Thus the low toxicity and excellent cellular uptake of ACBC followed by LSK1-38, makes these compounds prime choices as agents for BNCT therapy.

TABLE 2

Compounds: 1. ACBC; 2. LSK 1-38; 3. CN-V-264; 4. CDU-4

| Compound | Boron in cell (μg B/cell) | Atoms of $^{10}B$ (atoms $^{10}B$/cell) | Average number of interactions per cell from hand and computer calculations (Hand) | (Computer) | Dose calculation from hand and computer calculations (Hand) | (Computer) |
|---|---|---|---|---|---|---|
| 1 | $246.5 \times 10^3$ | $2749 \times 10^9$ | 50 | 68.5 | .44 | .197 |
| 2 | $8.6 \times 10^3$ | $96 \times 10^9$ | 1.7 | 2.7 | .013 | .014 |
| 3 | $4.5 \times 10^3$ | $50 \times 10^9$ | 0.9 | 1.0 | .0055 | .001 |
| 4 | $.9 \times 10^3$ | $10 \times 10^9$ | .18 | 0.0 | .0014 | .000 |

Thus, the boron-containing amino carboxylic acid compounds of this invention show effectiveness in delivering boron to glioblastoma multiforme tumors.

The tumor cell lines used herein were models. It is evident that other cell lines can be treated in a similar manner, such as C6 Glioma, U87 Glioblastoma, GM 2008 B mutant (skin fibroblast), GM 3348 B mutant (skin fibroblast), R1F sarcoma, B16 melanoma, U87, P-98, and F98 glioma cells.

Those skilled in the art will understand that many variations can be made in the compounds and methods described herein while still remaining within the bounds of the present invention. It is intended that such variations should be included within the scope of the invention as defined within the following claims.

What is claimed is:

1. A boron-containing aminocycloalkane having the formula:

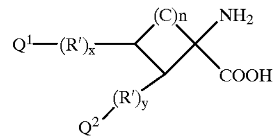

wherein n is 1 or 2;

wherein $Q^1$ and $Q^2$ are hydrogen, or a boron substituent selected from the group consisting of closo- and nido-polyhedral borane, carborane, boronic acid and its esters, boron hydride, and pharmaceutically acceptable water-soluble salts thereof with the proviso that $Q^1$ and $Q^2$ are not H concurrently, wherein said boron substituent is linked to said aminocycloalkane by a radical (R') which is selected from the group consisting of alkyl containing 1 to 12 carbon atoms, alkenyl containing 1 to 12 carbon atoms, alkynyl containing 1 to 12 carbon atoms, and aryl groups;

wherein x is 0 or 1 and x=0 when $Q^1$=H;

wherein y is 0 or 1 and y=0 when $Q^2$=H; and wherein (R') linked to $Q^1$ is selected independently from (R') linked to $Q^2$.

2. A boron-containing compound which is 2-amino-5-(2-methyl-1,2-dicarba-closo-dodecacarboran (12)-1-yl) pentane carboxylic acid.

3. The boron-containing compound of claim 1 which is selected from the following: 1-amino-3-(2-(7-(2-hydroxyethyl)-1,7-dicarba-nido-dodecacarboran(12)-ylethyl) cyclobutanecarboxylic acid; amino-3-(2-(1-methyl-1,2-dicarba-closo-dodecacarboran(12)-1-yl) ethyl) cyclobutanecarboxylic acid; 1-amino-3(2-(7-(2-hydroxyethyl)-1,7-dicarba-closo-dodecacarboran(12)-ylethyl)cyclobutanecarboxylic acid; 1-amino-3-(2-(1,7-dicarba-closo-dodecacarboran(12)-1-yl)) ethylcyclobutane carboxylic acid and 1-amino-3-(2-(7-(2-hydroxyethyl)-1,7-dicarba-nido-dodecacarboran(12)-yl) ethyl) cyclobutanecarboxylic acid.

4. The boron-containing compound of claim 3 which is 1-amino-3-(2-(7-2-hydroxyethyl)-1,7-dicarba-nido-dodecacarbon(12)-yl)ethyl)cyclobutane carboxylic acid.

5. The boron-containing compound of claim 1 wherein the aminocycloalkane carboxylic acid is an aminocyclobutane carboxylic acid.

6. The boron-containing compound of claim 1 wherein $Q^2$ is hydrogen.

7. The boron-containing compound of claim 1 wherein the boron substitutent is boronic acid having the formula $—(CH_2)_n—B(OH)_2$ wherein n is an integer of 1 to 12.

8. The boron-containing compound of claim 1 wherein $Q^1$ is a carborane selected from the group consisting of ortho-carborane and meta-carborane, having the formulas respectively:

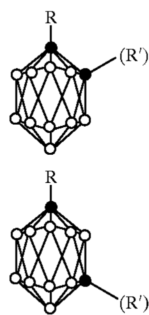

wherein R represents hydrogen, alkyl, alkenyl, alkynyl, aryl, alcopolyol, saccharide, peptide, hydroxy alkyl, hydroxy or thiol groups, and wherein R' represents alkyl, alkenyl, alkynyl, or aryl groups wherein alk is 1 to 6 carbon atoms, and aryl of 6 carbon atoms, and wherein O represents boron and • represents carbon.

9. The boron-containing compound of claim 8 wherein the carborane is meta-carborane.

10. The boron-containing compound of claim 8 wherein the carborane is ortho-carborane.

11. The boron-containing compound of claim 5 wherein $Q^2$ is $—(CH_2)_8—B(OH)_2$ and $Q^1$ is selected from the group consisting of closo- and nido-polyhedral borane, carborane, boronic acid, a boronic ester, and boron hydride.

12. A mixture of the compounds of claim 1 which is enriched in isotope $B^{10}$.

13. An optically pure D-enantiomer of racemates of the compounds of claim 1.

14. A method for chemically synthesizing a boron-containing aminocycloalkane carboxylic acid of claim 1, comprising the steps of:

alkylating a boron-containing group by reacting the group with 4-bromo-butene, reacting the alkylated boron-containing group with dichloroketene to obtain a dichloroketone of the alkylated boron-containing group, reducing the dichloroketone to remove chlorine and to obtain an alkylated boron-containing ketone, reacting the ketone with KCN to obtain an alkylated boron-containing hydantoin, and hydrolyzing the hydantoin to generate the boronated 1-aminocycloalkane carboxylic acid.

15. The method of claim 14 wherein the aminocycloalkane carboxylic acid is an aminocyclobutane carboxylic acid.

16. The boron-containing compound of claim 8 wherein R is selected from the group consisting of hydroxy, hydroxyethyl and methyl.

17. An optically pure L-enantiomer of racemates of the compounds of claim 1.

* * * * *